US012016572B2

(12) United States Patent
Fiedler et al.

(10) Patent No.: US 12,016,572 B2
(45) Date of Patent: Jun. 25, 2024

(54) MILLING DEVICE FOR PROSTHETIC SURGERY

(71) Applicant: LIMACORPORATE S.P.A, San Daniele del Friuli (IT)

(72) Inventors: Christoph Fiedler, Diekhof (DE); Massimo Ceconi, Travesio (IT)

(73) Assignee: LIMACORPORATE S.P.A, San Daniele del Friuli (IT)

( * ) Notice: Subject to any disclaimer, the term of this patent is extended or adjusted under 35 U.S.C. 154(b) by 423 days.

(21) Appl. No.: 17/601,690

(22) PCT Filed: Mar. 19, 2020

(86) PCT No.: PCT/IT2020/050065
§ 371 (c)(1),
(2) Date: Oct. 5, 2021

(87) PCT Pub. No.: WO2020/202227
PCT Pub. Date: Oct. 8, 2020

(65) Prior Publication Data
US 2022/0192682 A1 Jun. 23, 2022

(30) Foreign Application Priority Data
Apr. 5, 2019 (IT) .......................... 102019000005272

(51) Int. Cl.
*A61B 17/16* (2006.01)
*A61B 17/00* (2006.01)
*A61F 2/46* (2006.01)

(52) U.S. Cl.
CPC ...... *A61B 17/1617* (2013.01); *A61B 17/1631* (2013.01); *A61F 2/4603* (2013.01); *A61B 2017/00477* (2013.01); *A61B 2017/1602* (2013.01)

(58) Field of Classification Search
CPC ............ A61B 17/1617; A61B 17/1631; A61B 2017/00477; A61B 2017/1602; A61F 2/4603
See application file for complete search history.

(56) References Cited

U.S. PATENT DOCUMENTS

| 1,677,337 | A | * | 7/1928 | Grove | ............... | A61B 17/1688 |
| | | | | | | 606/180 |
| 9,078,672 | B1 | * | 7/2015 | Rosse | ............... | A61B 17/1631 |
| 2006/0217728 | A1 | * | 9/2006 | Chervitz | ............ | A61B 17/1757 |
| | | | | | | 606/79 |

(Continued)

FOREIGN PATENT DOCUMENTS

| CN | 107334507 A | 11/2017 |
| EP | 1410763 A1 | 4/2004 |

OTHER PUBLICATIONS

International Search Report and Written Opinion of PCT/IT2020/050065 dated Jul. 22, 2020 (15 pages).

*Primary Examiner* — Kevin T Truong
*Assistant Examiner* — Diana Jones
(74) *Attorney, Agent, or Firm* — Calfee, Halter & Griswold LLP

(57) ABSTRACT

Milling device for prosthetic surgery comprising a milling tool and a handler body. The handler body is provided with a rotating drive shaft which develops along a longitudinal axis of rotation and is connected to the milling tool to rotate the milling tool around the longitudinal axis.

20 Claims, 4 Drawing Sheets

(56) References Cited

U.S. PATENT DOCUMENTS

| | | | |
|---|---|---|---|
| 2007/0225720 A1* | 9/2007 | Wolford | F16D 3/08 |
| | | | 606/80 |
| 2007/0293869 A1* | 12/2007 | Conte | A61B 17/1666 |
| | | | 606/91 |
| 2008/0058804 A1* | 3/2008 | Lechot | A61B 17/1631 |
| | | | 606/53 |
| 2011/0152867 A1* | 6/2011 | Petrzelka | A61B 17/808 |
| | | | 227/175.1 |
| 2012/0232558 A1* | 9/2012 | Berberich | A61B 17/1604 |
| | | | 606/84 |
| 2015/0354635 A1* | 12/2015 | Mcclymont | A61B 17/1631 |
| | | | 408/126 |
| 2017/0071631 A1* | 3/2017 | Phillips | A61B 17/1633 |

* cited by examiner

MILLING DEVICE FOR PROSTHETIC SURGERY

CROSS-REFERENCE TO RELATED APPLICATIONS

This application is a 371 Application of PCT/IT2020/050065, filed on Mar. 19, 2020, which claims priority to Italian Application No. 102019000005272, filed on Apr. 5, 2020, the contents of which are hereby incorporated by reference as if recited in their entirety.

FIELD OF THE INVENTION

The present invention concerns a milling device for prosthetic surgery suitable to prepare seatings for bone void fillers, or to prepare bone seatings to house a prosthesis.

In particular, the milling device is particularly suitable to make seatings for bone void fillers for a knee prosthesis, or to prepare a bone seating for a shoulder joint prosthesis, also called a humeral prosthesis, or for a hip prosthesis.

BACKGROUND OF THE INVENTION

It is known that in orthopedic surgery to implant a prosthesis, when the preparation of a seating for a bone void filler or the preparation of a housing seating for a prosthesis is required, it is necessary to make a hole in the bone and/or a milling in order to make the seating with the desired profile.

Often, in fact, congenital or traumatic degenerative pathologies, for example primary arthrosis, secondary arthrosis due to a trauma or caused by infections, rheumatoid arthritis, inflammatory arthritis, osteonecrosis, or bone tumors, or other similar problems, require the implantation of a prosthesis able to reproduce, overall, a movement that is analogous to that of the healthy joint.

It is also known that when, due to the pathologies as above, the cancellous bone cannot support the prosthesis, it is necessary to make suitable bone seatings for the implantation of a bone or metal void filler that acts as a support for the prosthesis. This problem can become critical especially for knee prostheses and for hip and shoulder prostheses.

The knee prosthesis typically comprises a femoral component, which is attached to the distal end of the femur, and a tibial component, which is attached to the proximal end of the tibia.

Especially if it is necessary to perform a revision of a previously implanted knee prosthesis, making a bone seating to apply suitable support cones first requires making a hole with one or more reamer devices with increasing diameter, and subsequently shaping it with a suitable milling device.

For this purpose, the milling devices which can be used during prosthetic surgery to prepare the seatings as above are known.

These milling devices typically comprise a handler body provided with a shaft which develops along a longitudinal axis, substantially coinciding with the axis of the intra medullary canal, depending on the case, of the tibia or femur, and provided with a proximal end which has an attachment to a drive member and a distal end connected to a milling tool, rotated by the drive member.

Since both tibia and femur have an asymmetrical elongated conformation, one of the main problems encountered during the preparation of a bone seating is avoiding perforation of the cortical zone of the tibial and femoral bone.

One of the disadvantages of known milling devices is that they are configured to shape the bone seating in the direction of a milling axis which substantially coincides with the axis of the intra medullary canal, depending on the case, of the tibia or femur, therefore being unable to follow the anatomy of the tibial and femoral bone.

Sometimes, in order to avoid perforation of the cortical zone, the surgeon is therefore forced to make bone seatings with a limited size which, however, may not be sufficient to guarantee an adequate joint stability of the prosthesis, especially in the event previous implants of prostheses have damaged, or in any case rendered unusable, an extended zone of the cancellous bone.

There is therefore the need to perfect a milling device for prosthetic surgery that can overcome at least one of the disadvantages of the state of the art.

In particular, one purpose of the present invention is to provide a milling device for prosthetic surgery that is able to perform a milling avoiding damage to the cortical zone of the bone.

Another purpose of the present invention is to provide a milling device for prosthetic surgery which is able to produce a stable milling with respect to a milling axis that is different from the axis of the intra medullary canal, that is, different from the axis of the guided shaft which is inserted inside it.

Another purpose of the present invention is to provide a milling device for prosthetic surgery which is simple to use, and which consists of a limited number of components.

Another purpose of the present invention is to provide a milling device for prosthetic surgery that is simple to assemble, to perform the surgical operation, and disassemble, to carry out its cleaning and sterilization.

The Applicant has devised, tested and embodied the present invention to overcome the shortcomings of the state of the art and to obtain these and other purposes and advantages.

SUMMARY OF THE INVENTION

The present invention is set forth and characterized in the independent claim. The dependent claims describe other characteristics of the present invention or variants to the main inventive idea.

In accordance with the above purposes, the milling device for prosthetic surgery comprises a milling tool and a handler body that has a rotating drive shaft which develops along a longitudinal axis. The rotating shaft is connected to the milling tool to rotate the milling tool around the longitudinal axis.

In accordance with one aspect of the present invention, the rotating shaft comprises an angular joint rotatably coupled with the milling tool to selectively define a plurality of inclined positions of the milling tool with respect to the longitudinal axis.

In accordance with another aspect of the present invention, the handler body comprises a guide member which comprises a stabilizer body disposed eccentric with respect to the longitudinal axis, configured to cooperate with the milling tool so as to selectively define, amongst the plurality of inclined positions as above, a single specific stable inclined position of the milling tool with respect to the longitudinal axis.

BRIEF DESCRIPTION OF THE DRAWINGS

These and other aspects, characteristics and advantages of the present invention will become apparent from the following description of some embodiments, given as a non-limiting example with reference to the attached drawings wherein.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

Figure 1:
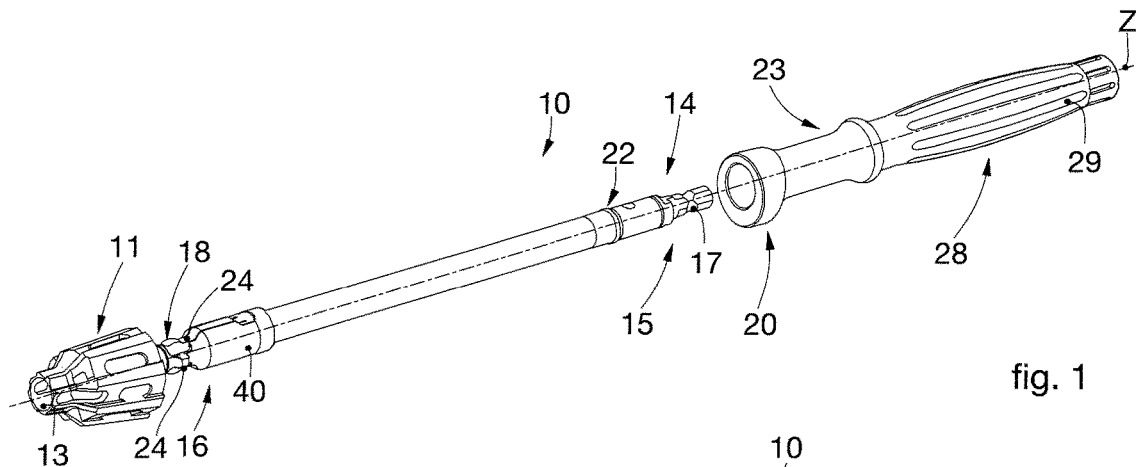
FIG. 1 shows an exploded perspective view of a milling device for prosthetic surgery, in particular for application to the tibial bone, in accordance with embodiments described herein.

We will now refer in detail to the various embodiments of the invention, of which one or more examples are shown in the attached drawings. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall include all such modifications and variants.

Before describing the embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

Embodiments described using the attached drawings concern a milling device for prosthetic surgery, indicated as a whole with reference number 10 in the attached drawings.

With particular reference to the attached drawings, FIGS. 1-9 concern a milling device 10 suitable to make seatings for bone void fillers for the tibial bone, FIGS. 10-13 concern a milling device 10 suitable to make seatings for bone void fillers for the femoral bone, and FIGS. 14-17 concern a milling device 10 suitable to making seatings for a shoulder joint prosthesis, also called a humeral prosthesis.

The milling device for prosthetic surgery 10, hereafter device 10, comprises a milling tool 11 and a handler body 14 with a rotating drive shaft 22 which develops along a longitudinal axis Z, connected to the milling tool 11 to rotate the milling tool 11 around the longitudinal axis Z.

In accordance with one aspect of the present invention, the rotating shaft 22 comprises an angular joint 18 rotatably coupled with the milling tool 11 to selectively define a plurality of inclined positions of the milling tool 11 with respect to the longitudinal axis Z.

In accordance with another aspect of the present invention, the handler body 14 comprises a guide member 20 which comprises a stabilizer body 21 disposed eccentric with respect to the longitudinal axis Z, configured to cooperate with the milling tool 11 so as to selectively define, amongst the plurality of inclined positions, a single specific stable inclined position of the milling tool 11 with respect to the longitudinal axis Z.

The specific stable inclined position allows the milling tool 11 to rotate with respect to a milling axis R inclined with respect to the longitudinal axis Z of rotation of the rotating shaft 22, by an angle of inclination α variable according to the surgical application (application to the tibial bone, to the femoral bone or to the shoulder joint). So it can be said that the milling tool 11 is inclined with respect to the rotating shaft 22 and to the handler body 14.

In particular, the guide member 20 defines the angle of inclination α so that when the shaft 22 rotates with respect to the longitudinal axis Z, the milling tool rotates with respect to the milling axis R.

Figure 5:
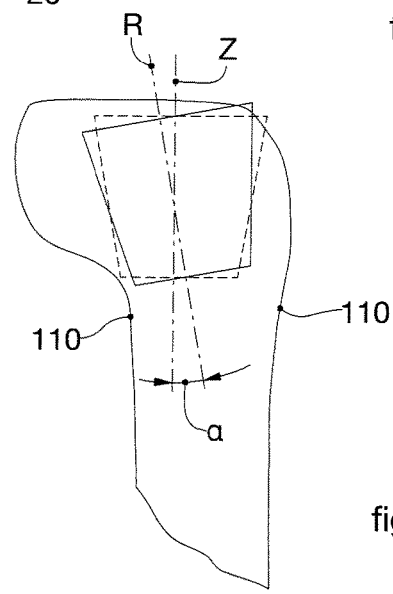
FIG. 5 shows a schematic view of a possible application of the milling device for prosthetic surgery and of the problem it resolves.
Figure 6:
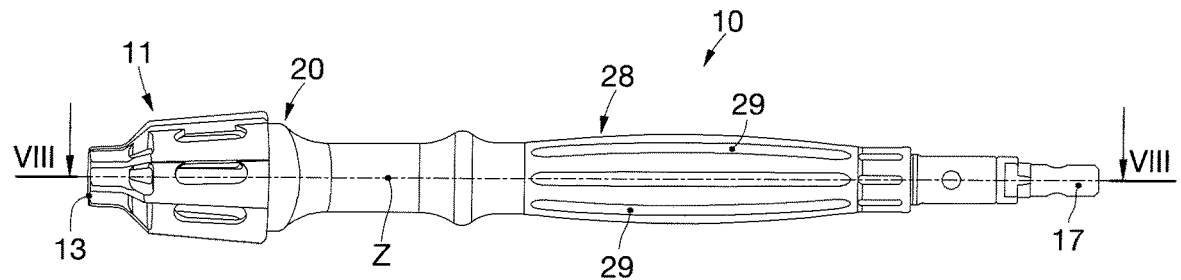
FIG. 6 shows a lateral view of a milling device for prosthetic surgery, in particular for application to the tibial bone, in accordance with embodiments described herein.
Figure 7:
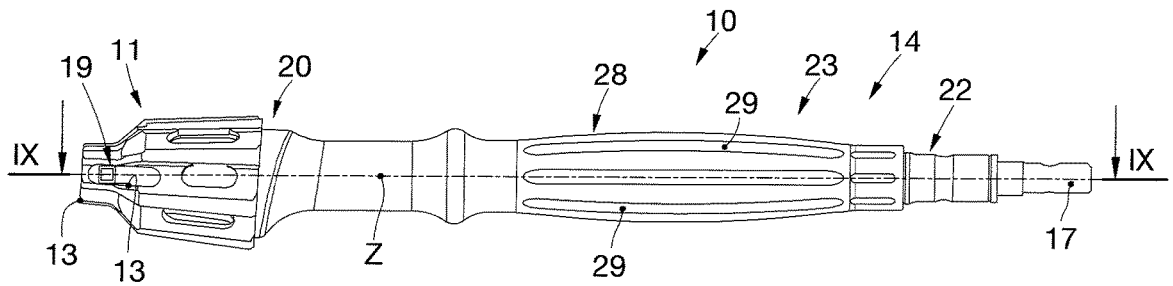
FIG. 7 is another lateral view of FIG. 6.
Figure 8:
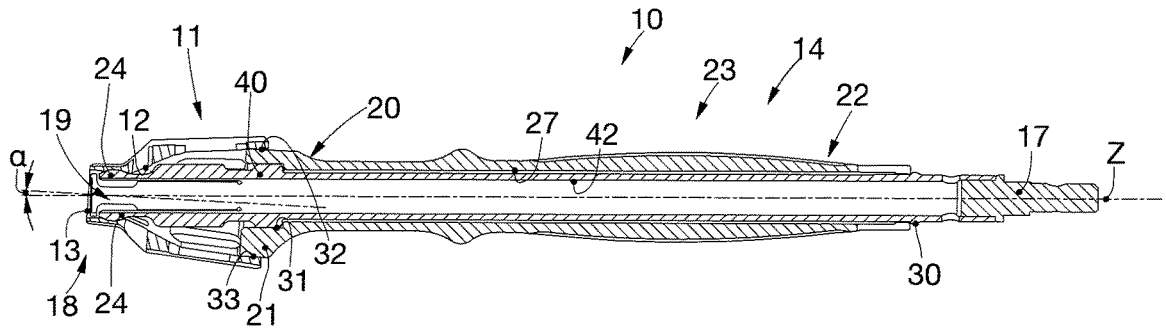
FIG. 8 is a section along line VIII-VIII of FIG. 6.
Figure 9:
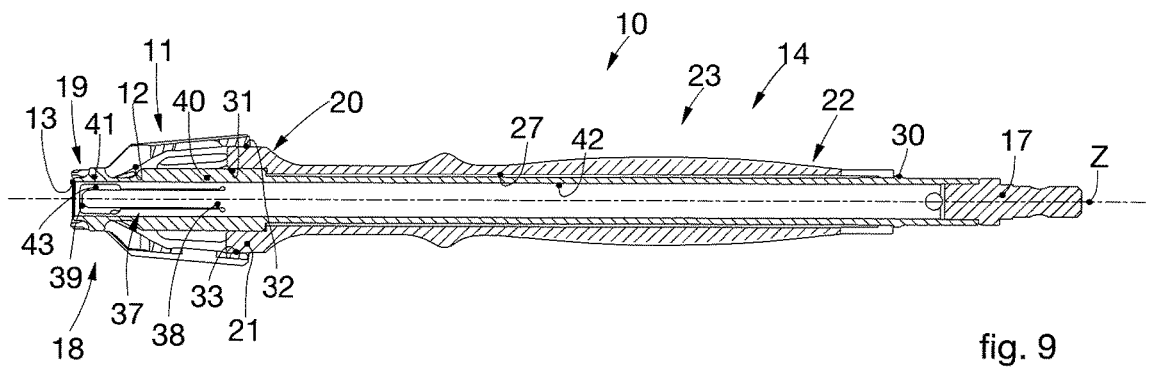
FIG. 9 is a section along line IX-IX of FIG. 7.

As shown schematically in FIG. 5, with this configuration of the device 10, it is possible to make a bone seating without damaging the cortical zone 110 of the bone. In fact, while overall the device 10 is used so that the longitudinal axis Z is substantially orthogonal to the tibial resection, that is, substantially parallel to the intra medullary canal, the device 10 shapes the bone seating with respect to the angle of inclination α which corresponds to the specific stable inclined position. Possibly, the milling tool 11 can have the profile of a rotating body obtained by the rotation of a desired curve, for example one that approximates the internal geometry of the tibia or femur. In particular, a known milling device is shown schematically with a dashed line, the device 10 in accordance with embodiments described herein is shown with a continuous line. Evidently, the known milling device moves much closer to the cortical zone 110 with the risk of damaging it.

In addition, this allows the user to make a deeper bone seating, being able to guarantee, especially in case of serious degeneration of the cancellous bone, a suitable joint stability of the prosthesis.

The milling tool 11 has a concave coupling seating 12 with a coupling polar aperture 13.

The shaft 22 is provided with a distal end 16 connected to the milling tool 11 inside the concave coupling seating 12, and a proximal end 15 which has an attachment 17 to a drive member to rotate the milling tool 11 around the longitudinal axis Z.

Here and in the following description, the relative terms "proximal" and "distal", when describing the shaft 22 of the milling device 10, are defined with reference to the perspective of the milling device 10. Therefore "proximal" refers to the direction of coupling with the attachment 17 and "distal" refers to the direction of coupling with the milling tool 11.

In particular, the angular joint 18 is positioned on the distal end 16 of the shaft 22, and is rotatably coupled with the coupling polar aperture 13 with degrees of freedom able to allow the milling tool 11 to selectively adopt a plurality of inclined positions with respect to the longitudinal axis Z.

According to embodiments, the handler body 14 comprises a tubular handle 23 coaxially coupled in a removable manner with the shaft 22 and provided with the guide member 20.

The tubular handle 23 is provided with a distal aperture 25 and a proximal aperture 26 respectively associated with the distal end 16 and the proximal end 15 of the shaft 22.

The tubular handle 23 has a through longitudinal channel 27 from the distal aperture 25 to the proximal aperture 26 for the rotational coupling with the shaft 22. Advantageously, the longitudinal channel 27 has a size in the direction orthogonal to the longitudinal axis Z greater than that of the shaft 22, this allows to prevent unwanted sliding.

In accordance with possible solutions, the tubular handle 23 can be made in one piece or it can be made in two separate shell-like parts selectively combinable to accommodate the shaft 22. Advantageously, the tubular handle 23 can be made of plastic material to reduce to a minimum the possible frictions with the shaft 22 and with the milling tool 11.

In accordance with embodiments described herein, with particular reference to FIGS. 8-9 and FIG. 13 and FIG. 17, the size of the proximal aperture 26 is slightly smaller than the size of the longitudinal channel 27 to cooperate with a circumferential retaining edge 30 of the shaft 22, and guarantee a desired positioning of the shaft 22 in the direction of the longitudinal axis Z.

Advantageously, the tubular handle 23 can have, externally, an ergonomic and non-slip grip 28 so that the user is aided in gripping and handling it. For this purpose, the tubular handle 23 has longitudinal grooves 29 which extend at least in a central zone thereof, possibly having knurled surfaces. In addition, the grip 28 can have a rounded shape in order to further improve its hold.

In accordance with embodiments described herein, the shaft 22 is cannulated, that is, it is internally hollow and has a guide channel 42 parallel to the longitudinal axis Z and suitable to accommodate a guide element necessary to axially position the device 10 in the desired milling position during surgery.

At least in the case of a milling device 10 for femoral and/or tibial bone, the guide element can generally be a reamer device which is used before the device 10 to create a first hole, or first holes of increasing diameters. Once the suitable diameter of the hole has been reached, the device 10 is prepared so that the guide element is inserted in the guide channel 42 and therefore acts as an axial guide for the milling operation.

The guide member 20, and in particular the stabilizer body 21, is configured to cooperate with the concave coupling seating 12.

According to embodiments, the stabilizer body 21 is configured to make a same-shape coupling with the concave coupling seating 12 of the milling tool 11, so as to define the specific stable inclined position of the milling tool 11 with respect to the longitudinal axis Z based on the eccentricity with respect to the longitudinal axis Z.

The guide member 20 comprises the distal aperture 25 and a sliding coupling seating 31 configured to accommodate a shaped portion 40 of the shaft 22, to guarantee a desired positioning of the shaft 22 in the direction of the longitudinal axis Z. In particular, the seating 31 is concentric with respect to the longitudinal axis Z.

The seating 31 is configured to perform a positioning action of the shaft 22 in cooperation with the positioning action performed by the circumferential retaining edge 30. In this way, once the shaft 22 is operatively inserted in the longitudinal channel 27, its positioning in the direction of the longitudinal axis Z is substantially determined. In particular, the shaped portion 40 is in a rotational coupling with the seating 31. This coupling presupposes that there is a minimum space between the surfaces of the seating 31 and the surfaces of the shaped portion 40 to allow a functional movement.

Figure 2:
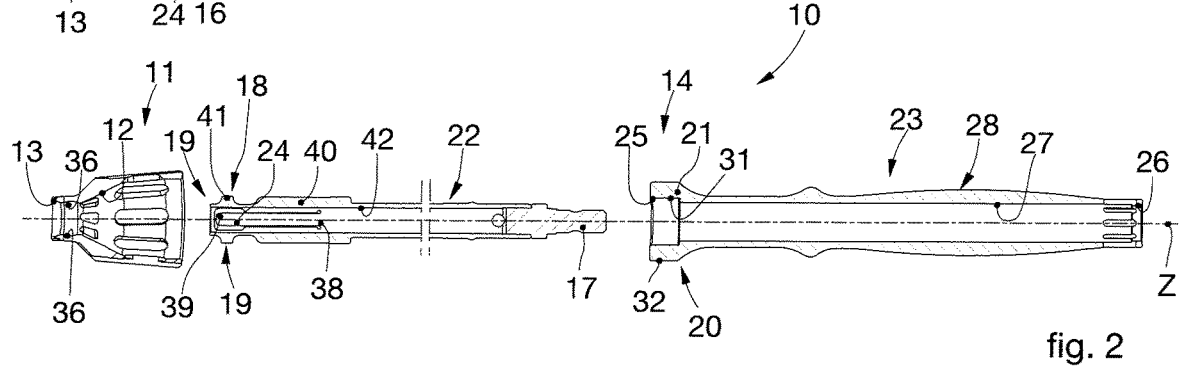
FIG. 2 shows a sectioned lateral elevation view of FIG. 1.
Figure 3:
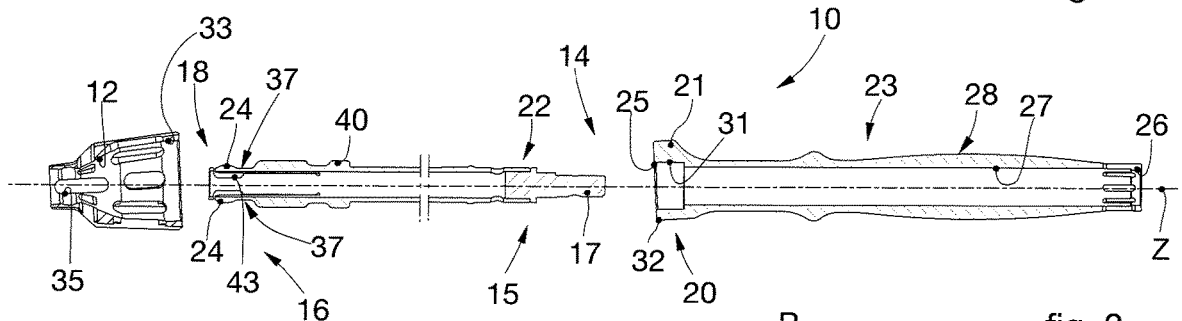
FIG. 3 shows another sectioned lateral elevation view of FIG. 1.
Figure 10:
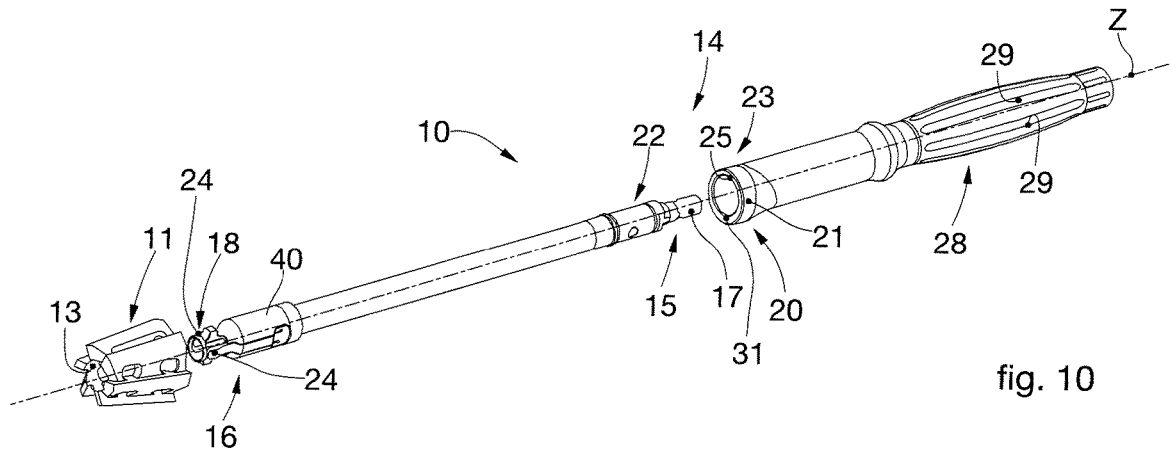
FIG. 10 shows an exploded perspective view of a milling device for prosthetic surgery, in particular for application to the femoral bone, in accordance with the embodiments described here.
Figure 11:
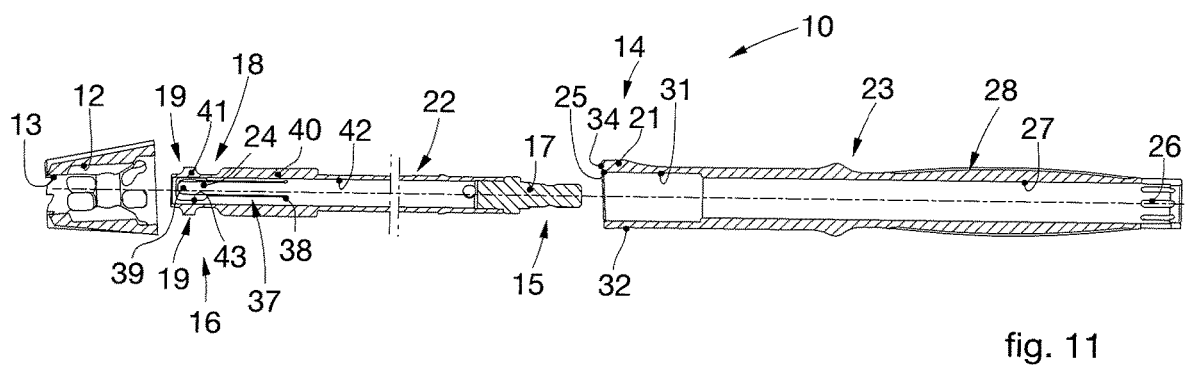
FIG. 11 shows a sectioned lateral elevation view of FIG. 10.
Figure 12:
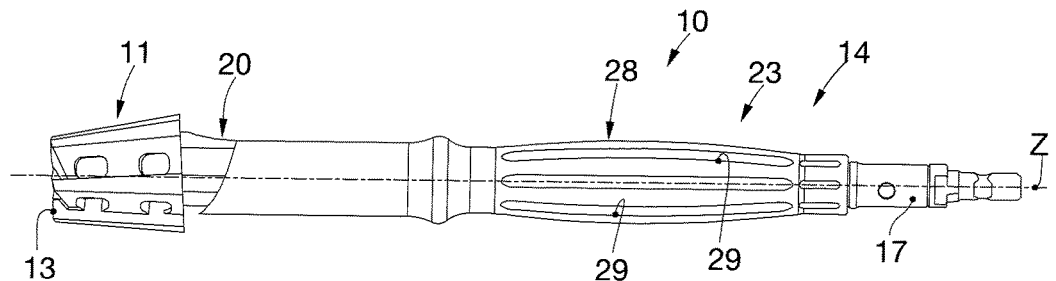
FIG. 12 shows a lateral view of a milling device for prosthetic surgery, in particular for application to the femoral bone, in accordance with the embodiments described herein.
Figure 13:
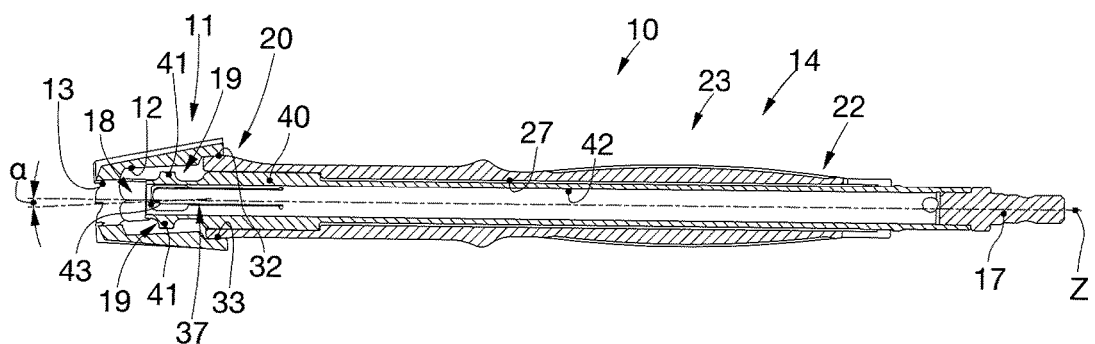
FIG. 13 is a longitudinal section of FIG. 12.

According to embodiments, for example shown in FIGS. 1-3 and in FIGS. 10-11, the shaped portion 40 has a substantially cylindrical shape. The stabilizer body 21 has an external surface 32 in sliding coupling with an internal surface 33 of the concave coupling seating 12 of the milling tool 11. The external surface 32 is defined by a cylindrical portion and is inclined with respect to the longitudinal axis Z by an angle of inclination α which substantially defines the angulation of the milling axis R with respect to the longitudinal axis Z. The internal surface 33 of the concave coupling seating 12 has an advantageously cylindrical profile with a diameter slightly larger than the diameter of the cylindrical portion that defines the external surface 32, to ensure the sliding coupling as above. The sliding coupling guarantees the single specific stable inclined position of the milling tool 11 with respect to the longitudinal axis Z.

The stabilizer body 21 also has a base surface 34 provided with the distal aperture 25, which allows access to the seating 31. The surface of the seating 31 and the external surface 32 are connected to the base surface 34, the first externally, the second internally with respect to the distal aperture 25. In particular, since the stabilizer body is disposed eccentric with respect to the longitudinal axis Z, the distal aperture 25 is not centered with respect to the base surface 34, but is concentric with the longitudinal axis Z.

Figure 4:
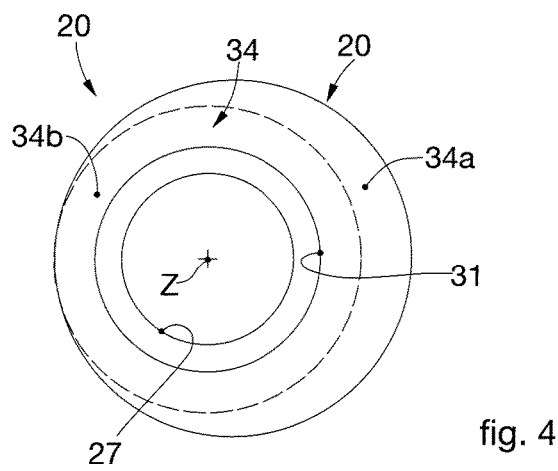
FIG. 4 shows a schematic plan view from above of a component of FIG. 1.

As schematically shown in FIG. 4, the base surface 34 is overall eccentric with respect to the longitudinal axis Z and is defined by a first concentric portion 34a, delimited solely for illustrative purposes with a dotted line, with respect to the longitudinal axis Z, and by a second portion 34b eccentric with respect to the longitudinal axis Z, the portions 34a, 34b being essentially one the continuation of the other. The larger the second portion 34b, and therefore the greater the eccentricity of the base surface 34, the greater the angle of inclination of the milling tool 11 with respect to the longitudinal axis Z in the stable inclined position.

The base surface 34 is inclined with respect to the longitudinal axis Z by an angle of inclination α which corresponds to the angle of inclination α of the single specific stable inclined position of the milling tool 11 with respect to the longitudinal axis Z. In the case of a milling device 10 for the preparation of a bone seating for a prosthesis of the knee joint, the angle of inclination α is about 5° for the milling device 10 for the tibial bone, and about 3° for the milling device 10 for the femoral bone.

Figure 14:
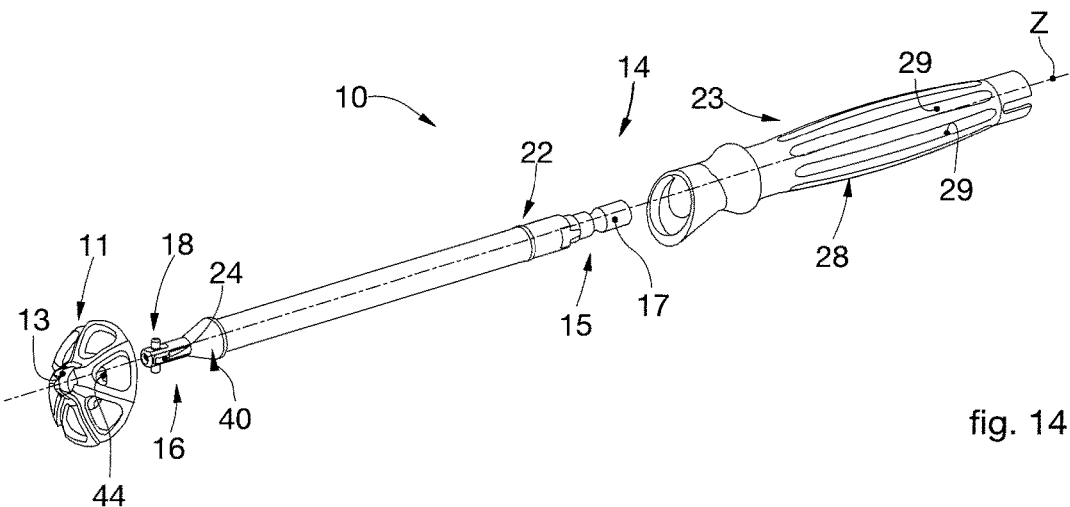
FIG. 14 shows an exploded perspective view of a milling device for prosthetic surgery, in particular for application to the shoulder joint, in particular for the glenoid, in accordance with embodiments described herein.
Figure 15:
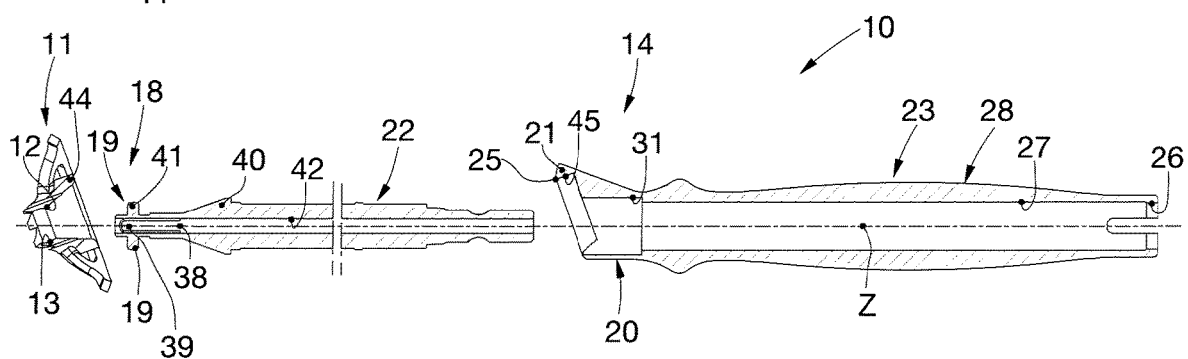
FIG. 15 shows a sectioned lateral elevation view of FIG. 14.
Figure 16:
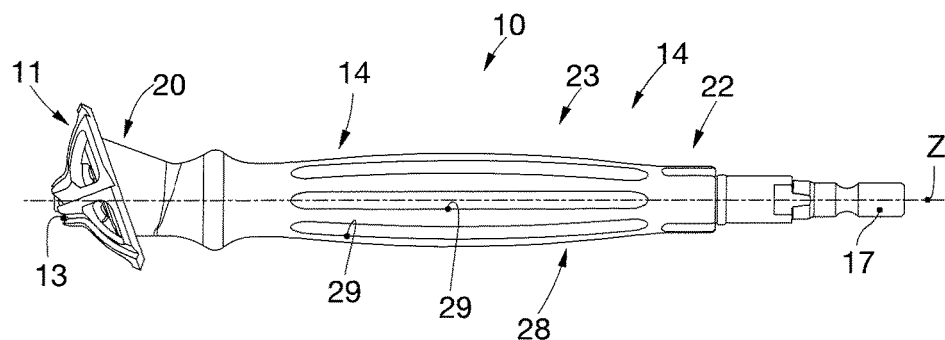
FIG. 16 shows a lateral view of a milling device for prosthetic surgery, in particular for application to the shoulder joint, in particular for the glenoid, in accordance with the embodiments described herein.
Figure 17:
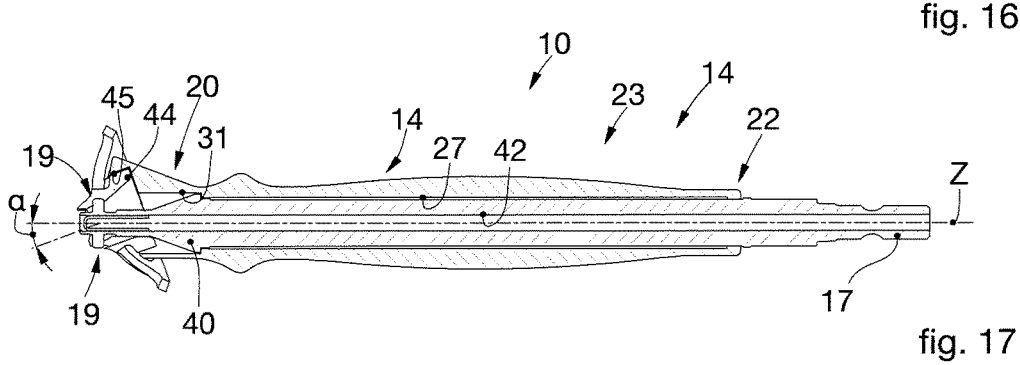
FIG. 17 is a longitudinal section of FIG. 16.

According to embodiments, shown in FIGS. 14-15, the shaped portion 40 has a substantially conical shape. Furthermore, the milling tool 11 is provided with a connection crown 44 in sliding coupling with an inclined seating 45 by an angle of inclination α which corresponds to the angle of inclination α of the single specific stable inclined position of the milling tool 11 with respect to the longitudinal axis Z. The sliding coupling guarantees the single specific stable inclined position of the milling tool 11 with respect to the longitudinal axis Z. In the case of a milling device 10 for the preparation of a bone seating for a prosthesis of a shoulder joint the angle of inclination α is approximately 25°.

According to embodiments, anti-rotation constraining elements 19 are present on the distal end 16 of the shaft 22 and are operatively coupled with coupling seatings 35 provided in the concave coupling seating 12 of the milling tool 11. The anti-rotation constraining elements 19 are configured to angularly constrain the milling tool 11 with respect to the handler body 14 so that they are able to rotate integrally around the longitudinal axis Z.

The anti-rotation constraining elements 19 comprise rigid transmission tabs 41 with a shape mating with corresponding coupling seatings 35 present on the milling tool 11, to transmit the rotational motion to the milling tool 11.

The anti-rotation constraining elements 19 protrude radially from the profile of the shaft 22, advantageously in a diametrically opposite position with respect to each other if more than one is present. Advantageously, in fact, there are two anti-rotation constraining elements 19 to guarantee a better transmission of the rotation torque from the shaft 22 to the milling tool 11. This diametrically opposite disposition of the two anti-rotation constraining elements 19 allows the milling tool to horizontally pivot on a plane orthogonal to the one passing through the anti-rotation constraining elements 19 so as to selectively adopt a plurality of positions inclined with respect to the longitudinal axis Z, and in particular to adopt a single specific stable inclined position defined by the same-shape coupling of the stabilizer body 21 with the concave coupling seating 12 of the milling tool.

The anti-rotation constraining elements 19 are removably keyed into the coupling seatings 35, made in correspondence with the polar coupling aperture 13 of the milling tool 11.

The coupling seatings 35 are substantially radial with respect to the longitudinal axis Z and are configured to guarantee the constraint necessary to transmit the rotation torque from the shaft 22 to the milling tool 11.

Advantageously, the coupling seatings 35 are in a number coherent with the number of anti-rotation constraining elements 19. This guarantees a univocal and determinate connection of the milling tool 11 on the shaft 22, preventing possible assembly errors.

According to embodiments, the angular joint 18 has one or more convex curved portions 24 disposed around the longitudinal axis Z.

Advantageously, the angular joint 18 has at least two convex curved portions 24 disposed diametrically opposite with respect to the longitudinal axis Z.

In accordance with the embodiments described herein, the anti-rotation constraining elements 19 are disposed around the longitudinal axis Z alternating with the convex curved portions 24.

The convex curved portions 24 protrude radially from the profile of the shaft 22 in a position diametrically opposite with respect to that of the anti-rotation constraining elements 19, and are configured to couple with respective shaped concavities 36, which have a shape mating with that of the convex curved portions 24.

Advantageously, the shaped concavities 36 allow an elastic snap-in coupling which univocally determines the axial position of the milling tool 11. In fact, when the milling tool 11 is coupled with the shaft 22, the convex curved portions 24 are removably forced to be associated with the shaped concavities 36.

Advantageously, the one or more convex curved portions 24 are sphere portions.

According to embodiments, the angular joint 18 comprises elastic keying tabs 37, each provided with one of the convex curved portions 24.

Each keying tab 37 has an extension in the direction of the longitudinal axis Z and has a tip 39 provided with the convex curved portion 24, and a base 38, opposite the tip 39, stably attached to the shaft 22. Advantageously, only the base 38 is stably attached to the shaft 22, so that the keying tab 37 can flex with respect to the base 38 when pressure is exerted on the tip 39.

The keying tab 37 can flex in an orthogonal direction to the longitudinal axis Z. For this purpose, the angular joint 18 has a chamber 43 orthogonally through in the shaft 22 and configured to allow the keying tabs 37 to flex at least during the coupling with the milling tool 11.

It is clear that modifications and/or additions of parts may be made to the milling tool for prosthetic surgery as described heretofore, without departing from the field and scope of the present invention.

It is also clear that, although the present invention has been described with reference to some specific examples, a person of skill in the art shall certainly be able to achieve many other equivalent forms of milling tool for prosthetic surgery, having the characteristics as set forth in the claims and hence all coming within the field of protection defined thereby.

In the following claims, the sole purpose of the references in brackets is to facilitate reading: they must not be considered as restrictive factors with regard to the field of protection claimed in the specific claims.

The invention claimed is:

1. Milling device for prosthetic surgery comprising:
   a milling tool;
   a handler body with a rotating drive shaft which develops along a longitudinal axis of rotation, connected to said milling tool to rotate said milling tool;
   wherein said rotating shaft is cannulated, being internally hollow and having a guide channel parallel to said longitudinal axis and having an axis coaxial to said longitudinal axis and extending through said milling tool and suitable to accommodate a guide element necessary to axially position the device in the desired milling position during surgery, wherein said rotating shaft comprises an angular joint rotatably coupled with said milling tool to selectively define a plurality of inclined positions of said milling tool with respect to said longitudinal axis, said handler body comprises a guide member which comprises a stabilizer body disposed eccentric with respect to said longitudinal axis, configured to cooperate with said milling tool so as to selectively define, amongst said plurality of inclined positions, a single specific stable inclined position of said milling tool, in which said milling tool is able to rotate on itself around a specific milling axis inclined with respect to said longitudinal axis, thereby said milling axis being inclined with respect to said axis of said guide channel.

2. Device as in claim 1, wherein said stabilizer body is configured to achieve a same-shape coupling with said milling tool, so as to define said single specific stable inclined position of said milling tool with respect to said longitudinal axis, according to the eccentricity with respect to said longitudinal axis.

3. Device as in claim 2, wherein said handler body comprises a tubular handle coaxially coupled in a removable manner with said shaft and comprising said guide member.

4. Device as in claim 3, further comprising anti-rotation constraining elements on a distal end of said shaft, operatively coupled with coupling seatings provided inside a concave coupling seating of said milling tool.

5. Device as in claim 4, wherein said angular joint has one or more convex curved portions disposed around said longitudinal axis.

6. Device as in claim 5, wherein said one or more convex curved portions are sphere portions.

7. Device as in claim 6, wherein said angular joint has at least two convex curved portions disposed diametrically opposite with respect to said longitudinal axis.

8. Device as in claim 7, wherein said angular joint comprises elastic keying tabs each provided with one of said convex curved portions.

9. Device as in claim 8, wherein said anti-rotation constraining elements are disposed around said longitudinal axis, alternating with said convex curved portions.

10. Device as in claim 9, wherein said anti-rotation constraining elements comprise rigid transmission tabs mating in shape with corresponding coupling seatings present on said milling tool, in order to transmit the rotational motion to the milling tool.

11. Device as in claim 10, wherein said stabilizer body has an external surface in sliding coupling with an internal surface of the concave coupling seating of the milling tool, said external surface being defined by a cylindrical portion and being inclined with respect to said longitudinal axis by an angle of inclination which substantially defines the angle of said milling axis with respect to the longitudinal axis, said internal surface of the concave coupling seating having a cylindrical profile with a diameter slightly greater than the diameter of said cylindrical portion which defines said external surface.

12. Device as in claim 1, wherein said handler body comprises a tubular handle coaxially coupled in a removable manner with said shaft and comprising said guide member.

13. Device as in claim 1, further comprising anti-rotation constraining elements on a distal end of said shaft, operatively coupled with coupling seatings provided inside a concave coupling seating of said milling tool.

14. Device as in claim 1, wherein said angular joint has one or more convex curved portions disposed around said longitudinal axis.

15. Device as in claim 14, wherein said one or more convex curved portions are sphere portions.

16. Device as in claim 14, wherein said angular joint has at least two convex curved portions disposed diametrically opposite with respect to said longitudinal axis.

17. Device as in claim 14, wherein said angular joint comprises elastic keying tabs each provided with one of said convex curved portions.

18. Device as in claim 14, wherein said anti-rotation constraining elements are disposed around said longitudinal axis, alternating with said convex curved portions.

19. Device as in claim 18, wherein said anti-rotation constraining elements comprise rigid transmission tabs mating in shape with corresponding coupling seatings present on said milling tool, in order to transmit the rotational motion to the milling tool.

20. Device as in claim 1, wherein said stabilizer body has an external surface in sliding coupling with an internal surface of the concave coupling seating of the milling tool, said external surface being defined by a cylindrical portion and being inclined with respect to said longitudinal axis by an angle of inclination which substantially defines the angle of said milling axis with respect to the longitudinal axis, said internal surface of the concave coupling seating having a cylindrical profile with a diameter slightly greater than the diameter of said cylindrical portion which defines said external surface.

* * * * *